United States Patent
Elvers et al.

(10) Patent No.: US 12,048,576 B2
(45) Date of Patent: Jul. 30, 2024

(54) METHOD AND APPARATUS FOR GENERATING A PANORAMIC LAYER IMAGE

(71) Applicants: DENTSPLY SIRONA Inc., York, PA (US); SIRONA DENTAL SYSTEMS GMBH, Bensheim (DE)

(72) Inventors: Michael Elvers, Darmstadt (DE); Ulrich Schulze-Ganzlin, Lorsch (DE); Stefan Eichner, Heidelberg (DE)

(73) Assignee: DENTSPLY SIRONA INC., York, PA (US)

( * ) Notice: Subject to any disclaimer, the term of this patent is extended or adjusted under 35 U.S.C. 154(b) by 318 days.

(21) Appl. No.: 17/605,644

(22) PCT Filed: Apr. 23, 2020

(86) PCT No.: PCT/EP2020/061261
§ 371 (c)(1),
(2) Date: Oct. 22, 2021

(87) PCT Pub. No.: WO2020/216812
PCT Pub. Date: Oct. 29, 2020

(65) Prior Publication Data
US 2022/0202382 A1 Jun. 30, 2022

(30) Foreign Application Priority Data
Apr. 26, 2019 (EP) .................................. 19171428

(51) Int. Cl.
*A61B 6/51* (2024.01)
*A61B 6/46* (2024.01)
(Continued)

(52) U.S. Cl.
CPC ................ *A61B 6/51* (2024.01); *A61B 6/469* (2013.01); *G06T 7/0012* (2013.01); *G06T 7/11* (2017.01);
(Continued)

(58) Field of Classification Search
CPC .. A61B 6/14; A61B 6/469; G06T 7/11; G06T 7/0012; G06T 2207/10116; G06T 2207/30036
See application file for complete search history.

(56) References Cited

U.S. PATENT DOCUMENTS

2009/0310845 A1* 12/2009 Ogawa ..................... A61B 6/14
382/132
2015/0164446 A1* 6/2015 Toimela ................... A61B 6/14
378/39
(Continued)

FOREIGN PATENT DOCUMENTS

DE  10016678 A1  10/2001
DE  102008008733 A1  8/2009
(Continued)

OTHER PUBLICATIONS

International Search Report; PCT/EP2020/061261; Jun. 18, 2020 (completed); Jun. 26, 2020 (mailed).
(Continued)

*Primary Examiner* — David P Porta
*Assistant Examiner* — Fani Polyzos Boosalis
(74) *Attorney, Agent, or Firm* — DENTSPLY SIRONA INC.

(57) ABSTRACT

A method for generating a panoramic layer image of an object to be imaged, by employing a 2D panoramic X-ray device, the object being imaged by projecting X-rays generated by an X-ray source through the object in a projection direction and recording the X-rays with an X-ray detector.
(Continued)

Several 2D X-ray projection images are continuously recorded from various imaging directions while the X-ray source and the X-ray detector move around the object. At least one panoramic layer image is calculated from the recorded 2D X-ray projection images using a reconstruction method. The panoramic layer image is calculated by selecting and employing at least one partial area from at least two 2D X-ray projection images in relation to an active sensor area.

13 Claims, 3 Drawing Sheets

(51) Int. Cl.
*G06T 7/00* (2017.01)
*G06T 7/11* (2017.01)
(52) U.S. Cl.
CPC ............... *G06T 2207/10116* (2013.01); *G06T 2207/30036* (2013.01)

(56) References Cited

U.S. PATENT DOCUMENTS

2018/0122106 A1* 5/2018 Choi .................... H04N 23/698
2018/0322665 A1 11/2018 Loustauneau

FOREIGN PATENT DOCUMENTS

| EP | 0279294 A1 | 8/1988 |
| JP | 2007136163 A | 6/2007 |
| JP | 2016007338 A | 1/2016 |
| JP | 2016540600 A | 12/2016 |
| WO | 2015092119 A1 | 6/2015 |

OTHER PUBLICATIONS

International Preliminary Report on Patentability; PCT/EP2020/061261; Jun. 18, 2020 (completed); Jun. 26, 2020 (mailed).
Written Opinion of the International Searching Authority; PCT/EP2020/061261; Jun. 18, 2020 (completed); Jun. 26, 2020 (mailed).
Japanese Office Action dated Feb. 27, 2024.

* cited by examiner

METHOD AND APPARATUS FOR GENERATING A PANORAMIC LAYER IMAGE

CROSS-REFERENCE TO RELATED APPLICATIONS

This is a National Phase application of International Application No. PCT/EP2020/061261, filed Apr. 23, 2020, which claims the benefit of and priority to European Application Ser. No. 19171428.6, filed on Apr. 26, 2019, which are herein incorporated by reference for all purposes.

BACKGROUND

Technical Field

The invention relates to a device and a method for generating a panoramic layer image of an object to be imaged, wherein the object is imaged by projecting X-rays generated by an X-ray source through the object in a projection direction and recording said X-rays with an X-ray detector, wherein several 2D X-ray projection images are continuously recorded from various imaging directions while the X-ray source and the X-ray detector move around the object, wherein at least one panoramic layer image is calculated from the recorded 2D X-ray projection images by means of an algorithm.

Description of the Related Art

Several methods for generating panoramic layer images are known from the prior art.

WO 2015092119 A1 and US 20150164446 A1 relates to generating digital dental panoramic layer images from multiple frame images acquired during a dental panoramic imaging scan from various scanning directions around a patient's head. The panoramic image is calculated by using information around the position and orientation of the X-ray source and the X-ray detector at particular points in time.

DE 102008008733 A1 discloses a method for generating a virtual panoramic layer image from a 3D volume, wherein the object to be imaged is virtually irradiated with a virtual X-ray source and the virtually generated image is recorded by a virtual detector. Undesirable structures can be removed during virtual radiation.

A disadvantage of this method is that the panoramic image is corrected based on an elaborate procedure for taking unwanted structures into account that in particular requires a 3D volume to virtually irradiate the object as desired.

Calculating a virtual panoramic layer image therefore requires a 3D volume from which the objects of interest are virtually irradiated. The resolution of virtual panoramic layer images is frequently lower than for classic panoramic layer images; additional artifacts can also occur. Preparing the 3D volume frequently requires a higher radiation dose.

DE 10016678 A1 discloses a method for irradiating an object, wherein the examined object is irradiated such that interfering, highly-absorbing objects, such as metal fillings, minimize the interference for imaging the opposing half of the jaw.

EP 0 279 294 A1 discloses a dental X-ray diagnostic apparatus for preparing panoramic layer images of a patient's jaw. The specified method permits rendering a layer in the object, the center of which is normally the patient's jaw. The panoramic layer image is prepared by moving a radiation source-detector arrangement around an imaged object and by clocking the CCD detector lines with a frequency changed relative to the speed of motion in order to generate a layer image by blurring the portions lying outside of the focal layer.

A disadvantage of the specified method is that a correction of the panoramic layer image is frequently very elaborate or completely impossible with regard to unwanted overlaps.

The object of the present invention is to provide a method for generating a panoramic layer image that in a straightforward manner can adjust the parameters and therefore the image in order to avoid repeated imaging and to improve diagnostic capabilities.

SUMMARY OF THE INVENTION

The invention relates to a device and a method for generating a panoramic layer image of an object to be imaged, by employing a 2D panoramic X-ray device, wherein the object is imaged by projecting X-rays generated by an X-ray source through the object in an radiation direction and recording said X-rays with an X-ray detector, wherein several 2D X-ray projection images are continuously recorded from various imaging directions while the X-ray source and the X-ray detector move around the object, wherein at least one panoramic layer image is calculated from the recorded 2D X-ray projection images by means of a reconstruction method. The panoramic layer image is calculated by selecting at least one partial area of at least two 2D X-ray projection images in relation to an active sensor area and using these for the calculation.

A panoramic layer image is a two-dimensional X-ray image of the upper jaw and/or the lower jaw that is recorded with a 2D panoramic X-ray device. The panoramic X-ray device can for example comprise an imaging unit with an X-ray detector, wherein the latter describes a movement around the patient's head during the imaging process. Synchronously on the opposite side thereto, the X-ray source moves around the patient's head. The X-ray source is designed to radiate a spatially restricted beam of X-rays that for example expands from an approximate width of 0.25 mm to an approximate width of 3 mm at the X-ray detector. This beam irradiates the jaw sections of the object, causing the 2D X-ray projection images of the different jaw sections of the entire jaw to be recorded frame by frame on the X-ray detector. A reconstruction method is then used to calculate a panoramic layer image from the recorded 2D X-ray projection images by assembling or computationally modeling the individual 2D X-ray projection images. The process of assembling the individual 2D X-ray projection images generates a focal layer of the panoramic layer images, said focal layer clearly showing anatomic structures located therein. This focus layer generally comprises the principal anatomic structures of the upper jaw and/or the lower jaw, such as teeth, tooth roots, and the jaw bones. The position/shape of the focal layer is determined by the path observed by the X-ray detector and the X-ray source in relation to the imaged object. The anatomic structures not located in the focal layer generate a shadow and are blurred out. The location of the focal layer is therefore determined by this path and the movements observed by the X-ray detector and by the X-ray source relative to the scanned object, wherein the width of the focal layers is additionally determined by the width of the irradiated area of the X-ray detector and/or by the width of the particular 2D X-ray projection images. A narrower width of the X-ray detector results in a wider focal layer and a wider X-ray detector results in a narrower focal layer while at the same time adjusting the beam to the X-ray detector width.

The present method therefore does not only calculate the panoramic layer image by using the complete 2D X-ray projection images in relation to the active sensor size, but also by merely selecting and using at least a partial area of these 2D X-ray projection images for the calculation. A smaller, arbitrarily shaped X-ray detector is therefore essentially simulated by selecting the at least one partial area.

An advantage of this method is that selecting the at least one partial area of the individual 2D X-ray projection images allows the width of the focal layer and also the radiation angle to be influenced by predetermined criteria. The individual partial areas of the 2D X-ray projection images can therefore be selected such that unfavorable overlaps within the focal layers of the panoramic layer image, for example of teeth and/or tooth crowns, are reduced and the principal anatomic structures, such as teeth and tooth roots, are rendered better.

Yet another advantage of the method is that the method is executed without the need for novel devices, but can instead be based on a conventional 2D panoramic X-ray device, wherein only the software is used to select the at least one partial area of the recorded 2D X-ray projection images in order to calculate a second panoramic layer image.

Yet another advantage of the method is that limiting the projection information used to reconstruct the panoramic layer image permits opening the inter-dental contacts, thus improving a dentist's diagnostic capabilities and reducing the number of repeat imaging procedures.

The X-ray detector can for example comprise a CMOS detector or a directly-converting detector having a width from 1 cm to 4 cm.

300 to 5000 2D X-ray projection images can for example be recorded while the X-ray detector moves around the object. This for example involves recording 50-1000.2D X-ray projection images per second.

The size of the partial area can advantageously comprise a maximum of 80% of the particular 2D X-ray projection image.

Relatively large partial areas of the 2D X-ray projection images are selected as a result. The at least one partial area can then comprise various shapes, such as an individual vertical stripe, a diagonally oriented stripe, or a stripe of variable width. When several partial areas are used, these can be positioned arbitrarily to each other, for example with a horizontal offset. Several partial areas of an individual 2D X-ray projection image can for example be several parallel, vertical stripes.

Selecting a smaller partial area on a side of the particular 2D X-ray projection image therefore increases the width of the focal layer and accordingly shifts a main radiation direction. A partial area with a variable width also allows the width of the focal layer to be locally varied within the panoramic layer image.

Advantageously, the size of the at least one partial area can comprise at most 40% of the active area of the particular 2D X-ray projection image.

As a result, relatively small partial areas are selected and used for calculating the panoramic layer image, thus changing or manipulating the panoramic layer image with greater effect.

Advantageously, a weighting function can be applied on the image data of the at least one selected partial area, wherein the weighted partial areas are used for calculating the panoramic layer image.

A Gauss function can for example be used as the weighting function. Image data in the center of the selected partial areas are then assigned a higher weight than the perimeter areas.

Advantageously, the partial area can be a partial stripe having a fixed width or a variable width.

By selecting a vertical partial stripe, each of the 2D X-ray projection images can for example be split into 40 partial stripes that can also be arranged with an overlap, so that for each individual partial stripe an individual panoramic layer image can be calculated that has a deviating main radiation direction. Consequently, for example 40 different panoramic layer images with variable main radiation directions can then be calculated from the same 2D X-ray projection images.

For a partial stripe with a variable width, for example the width can be reduced in the upper and lower area of the partial stripe and widened in the center area of the partial stripe, so that the width of the focal layer in the center area of the two jaws—e.g. in the area of the occlusal surfaces—is reduced in the second panoramic layer image, thus showing in particular the teeth in focus. The width of the focal layer is larger in the upper and lower area of the panoramic layer image so that objects arranged in the focal layer—such as the jaw bone and the tooth roots—are shown with less separation since other adjacent anatomical structures are also located within the focal layer, thus becoming more readily identifiable.

Advantageously, the at least one partial area can be selected manually by a user or automatically by employing an algorithm.

A user can therefore manually select the at least one partial area. The user can for example directly determine the at least one partial area, wherein then automatically based on these inputs, the corresponding partial areas within the 2D X-ray projection images are automatically selected by the computer. The user can also define a desired main radiation direction, for example in a contact area between two teeth, wherein the partial areas required for the reconstruction are then automatically determined by the computer in order to adjust the main radiation direction.

The partial areas can also be selected fully automatically, wherein the position/shape and width of the focal layer and the arrangement of the main radiation directions on the contact points between the individual teeth are determined automatically based on a reference head or based on prior knowledge, such as a 3D model of the upper and/or lower jaw, wherein the partial areas are then determined based on these inputs in order to calculate the desired panoramic layer image.

Advantageously, the selection of at least one partial area within the 2D X-ray projection images allows a width of a focal layer of the calculated panoramic layer image to be changed.

This influences the width of the focal layer by selecting the partial areas.

Advantageously, selecting at least one partial area within the 2D X-ray projection images allows the adjustment of at least one main radiation direction of the particular 2D X-ray projection image and therefore an adjustment of a main radiation direction to an associated position of the focal layer of the calculated panoramic layer image.

Selecting the at least one partial area then adjusts a main radiation direction of the calculated panoramic layer image. For example, if a partial stripe is selected on the left of the 2D X-ray projection images of the contact point between two molars and a panoramic layer image is calculated from the selected partial stripe, the main radiation direction on the contact location between the two molars is also shifted. In this manner, for example an opening can occur on the particular inter-dental contact on the contact points between the two molars, thus reducing an overlap of the molars in the panoramic layer image as much as possible.

Advantageously, the adjustment of the main radiation direction of the particular 2D X-ray projection images and therefore of the main radiation direction of the focal layer and/or the adjustment of the width of the focal layer can be made as a function of the anatomical structures of the object to be imaged.

The main radiation direction and the width of the focal layers are therefore adjusted as a function of the anatomical structures of the object to be imaged, that is to say the two jaws. For example, a 3D model from an optical 3D image of the two jaws can be relied on for this purpose, wherein the width of the focal layer and the main radiation directions can be determined on the contact points between the teeth as a function of the shape and extent of the upper and/or lower jaw.

Advantageously, the adjustment of the main radiation direction of the particular 2D X-ray projection images and therefore the adjustment of the main radiation direction of the focal layer can be made toward the opening of inter-dental contacts, wherein contact point between the teeth are determined and pre-defined and an appropriate center optimized radiation direction is determined for the particular position of the focal layer, such that the teeth have the lowest possible, or no, overlaps in the particular contact point within the calculated panoramic layer image.

Certain optimized radiation directions are thereby determined for the individual contact points between the teeth, and, as a function thereof, a second panoramic layer image is calculated, wherein the overlaps of the teeth at the contact points are minimized as much as possible.

Advantageously, a first panoramic layer image can be calculated from the individual 2D X-ray projection images, wherein the complete image information of the complete active sensor area of the 2D X-ray projection images is used for the calculation, wherein a second panoramic layer image is calculated from the selected partial areas of the 2D X-ray projection images.

The first panoramic layer image is thereby calculated from the complete 2D X-ray projection images, wherein the second panoramic layer image is calculated from the selected partial areas.

Advantageously, a difference between an actual radiation direction of the first panoramic layer image and a optimised radiation direction of the second panoramic layer images can be used to automatically determine tooth misalignments and to highlight these in a graphical rendering of the first and/or second panoramic layer image.

The difference between the actual radiation direction of the panoramic layer image and the optimised radiation direction of the second panoramic layer image is thereby indicated, so that it becomes evident at what locations the radiation direction was changed to reduce overlaps between the teeth at the contact points.

The optimized radiation direction on the inter-dental contacts and/or the contact points between the individual teeth can be determined manually by the user or automatically by a computer, wherein the individual teeth can be segmented and the particular contact point can be analyzed. This involves determining an optimized radiation direction under the scope of the radiation beam of the X-rays of the individual 2D X-ray projection images that results in the lowest possible overlap of the teeth along the contact points in a second calculated panoramic layer image.

Advantageously, a user can employ a control apparatus to toggle between a graphical rendering of the first panoramic layer image and the second panoramic layer image.

The user can thereby arbitrarily toggle between the first panoramic layer image and the second panoramic layer image. The first panoramic layer image and the second panoramic layer image can also be displayed simultaneously with a display apparatus.

Advantageously, a user can use a control apparatus to select an area in a graphical rendering of the first panoramic layer image, wherein a magnified rendering of this area from the second panoramic layer image is superimposed in the manner of a magnifying glass function.

The user can thereby select a certain area in the first panoramic layer image, such as a certain contact point between two teeth, so that this area is superimposed in the manner of a magnifying glass function from the second panoramic layer image with opened inter-dental contacts. In this manner, the user is then shown the conventional panoramic layer image, with the additional function that an opening of the inter-dental contact is permitted on the contact points with overlaps.

The invention further relates to an apparatus for executing the aforementioned method, comprising a computer, the X-ray source, the X-ray detector, a support arm for moving the X-ray source and the X-ray detector around the object to be imaged. The X-ray detector in this case has a width of at least 5 mm, wherein the computer employs a selection algorithm to select at least one partial area within the 2D X-ray projection image and then employs a calculation algorithm to calculate the panoramic layer image.

The apparatus to execute the aforementioned method therefore comprises the elements of a conventional 2D panoramic X-ray apparatus and a computer. The X-ray detector can also have a width between 5 mm and 40 mm, so that the location of the partial areas can be selected with greater flexibility.

An advantage of the apparatus is that only at least two conventional, corresponding 2D X-ray projection images of a panoramic layer image and a computer are sufficient to execute the present method. The software in this case only performs the selection of the at least one partial area in the 2D X-ray projection images and the calculation of the second panoramic layer image.

BRIEF DESCRIPTION OF THE DRAWINGS

The invention is explained based on the drawings. These show in

FIG. 1 a sketch for illustrating an embodiment of the present method, in

DETAILED DESCRIPTION OF THE INVENTION

Figure 1:
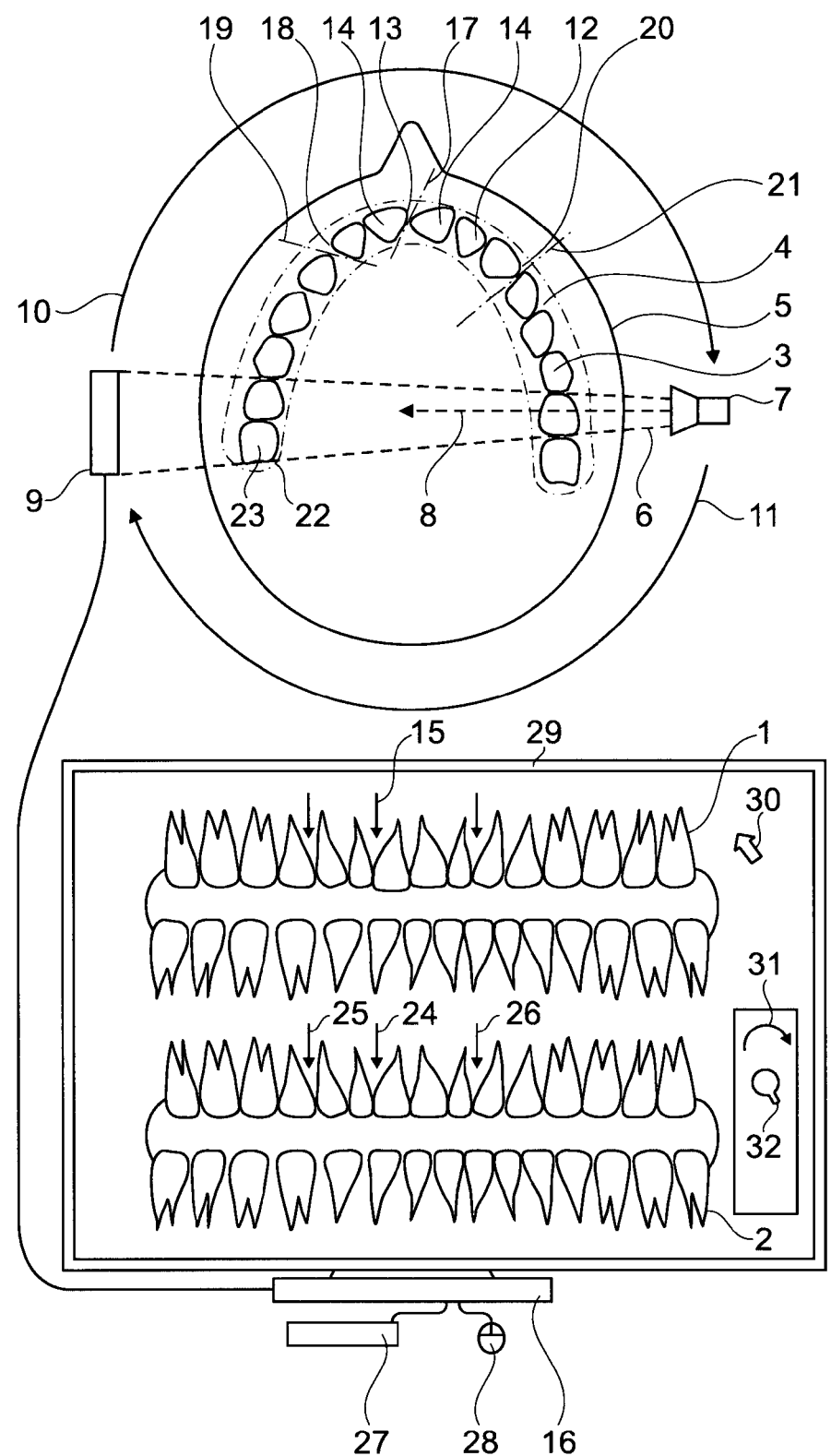

FIG. 1 shows a sketch for illustrating an embodiment of the present invention for generating a first panoramic layer image 1 and a second panoramic layer image 2 of an imaged object 3, wherein the beam of X-rays 6, represented as a dotted line, that irradiates the jaw 4 of the patient's head 5 is generated by an X-ray source 7, wherein the object is irradiated along a main radiation direction 8 of the beam of the X-rays 6. The X-rays 6 then impact an X-ray detector 9, such as a CMOS detector, and are recorded by the latter. During the imaging procedure, the X-ray detector 9 is for example continuously moved around the object 3, as indicated by arrow 10. This involves recording individual 2D X-ray projection images from different imaging directions and/or main radiation directions. Synchronously to the X-ray detector 9, the X-ray source 7 is mounted at opposite side and is accordingly moved along a circumferential path around the head 5 of the patient, as indicated by arrow 11.

For example 500 2D X-ray projection images can be recorded in the course of a circumferential path 10. The main radiation direction 8 can for example be calculated as an average value of the individual directions of the beam of the X-rays 6. The individual 2D X-ray projection images are then used to calculate the first panoramic layer image 1, wherein the complete image information in relation to the active sensor area of the X-ray detector 9 is used.

In order to open overlapping inter-dental contacts, an available 3D model of the patient's head 5 can be analyzed, wherein the individual teeth 12 of the upper jaw and/or the lower jaw 4 are segmented, and optimized radiation directions optimized on the contact points are determined. On a first contact point 13 between the front incisors 14, an overlap of the teeth is present in the first panoramic layer image 1, as indicated by the arrow 15. A first center optimized radiation direction 17 is then determined by a computer 16. A second optimized radiation direction 19 is determined on a second contact point 18. A third optimized radiation direction 21 is determined on a third contact point 20. On the basis of the specified optimized radiation directions 17, 19, and 21 and on the basis of the position/shape of the focal layer 22, the computer 16 then calculates a selection of the partial areas of the 2D X-ray projection image, so that the second panoramic layer image 2 is calculated from the selected partial areas. The second panoramic layer image 2 in particular shows that the inter-dental contacts on the first contact point 13 between the front incisors 14 were opened on the second contact point 18 and on the third contact point 20, as indicated by the arrows 24, 25, and 26. The overlaps of the teeth on the contact points were reduced as much as possible. Data entry devices, such as a keyboard 27 and a mouse 28, are connected to the computer 16. A display apparatus 29, such as a monitor, is also connected to the computer 16 in order to graphically render the first calculated panoramic layer image 1 and the second panoramic layer image 2. The user can employ the data entry device 27 and 28 by means of a cursor 30 to navigate within the panoramic layer images 1 and 2. By employing a first virtual tool 31, the user can toggle back and forth between the rendering of the first panoramic layer image 1 and the second panoramic layer image 2. By employing a second virtual tool 32, the user can use a magnifying glass function, wherein the user can use the magnifying glass to select a certain area in the first panoramic layer image 1, such as contact points 13, 18, and 20, wherein this area is rendered enlarged from the second panoramic layer image 2.

Figure 2:
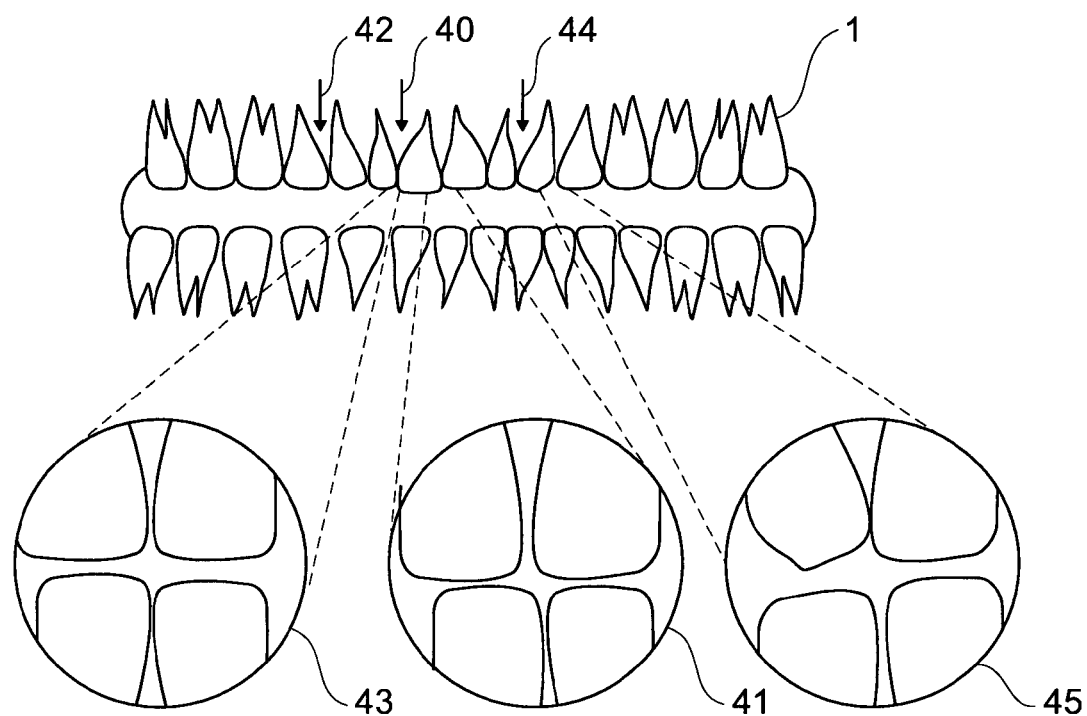
FIG. 2 a sketch of a magnifying glass function of the second virtual tool, in FIG. 3 a sketch of a 2D X-ray projection image with a partial stripe, in FIG. 4 a sketch of 2D X-ray projection image with a diagonal partial stripe, in FIG. 5 a sketch of a 2D X-ray projection image with two partial stripes, in FIG. 6 a sketch of a 2D X-ray projection image with a partial stripe having a variable width, in FIG. 7 a sketch of an X-ray detector comprising a frame and a sensor area.

FIG. 2 shows a sketch of a magnifying glass function of the second virtual tool 32 from FIG. 1, wherein the user—in the first panoramic layer image 1—selects a first overlapping area 40 on the position of the first contact point 13, which is rendered enlarged as section 41 from the second panoramic layer image 2. A second overlapping area 42 is correspondingly selected on the position of the second contact point 18 and rendered as a second section 43. A third overlapping area 44 is subsequently selected on the position of the third contact point 20 and rendered enlarged as a third section 45. The enlarged sections 41, 43, and 45 clearly show that the inter-dental contacts were opened on the contact points 13, 18, and 20, so that the overlaps within the first panoramic layer image 1 of teeth were reduced.

Figures 3, 4, 5, 6:
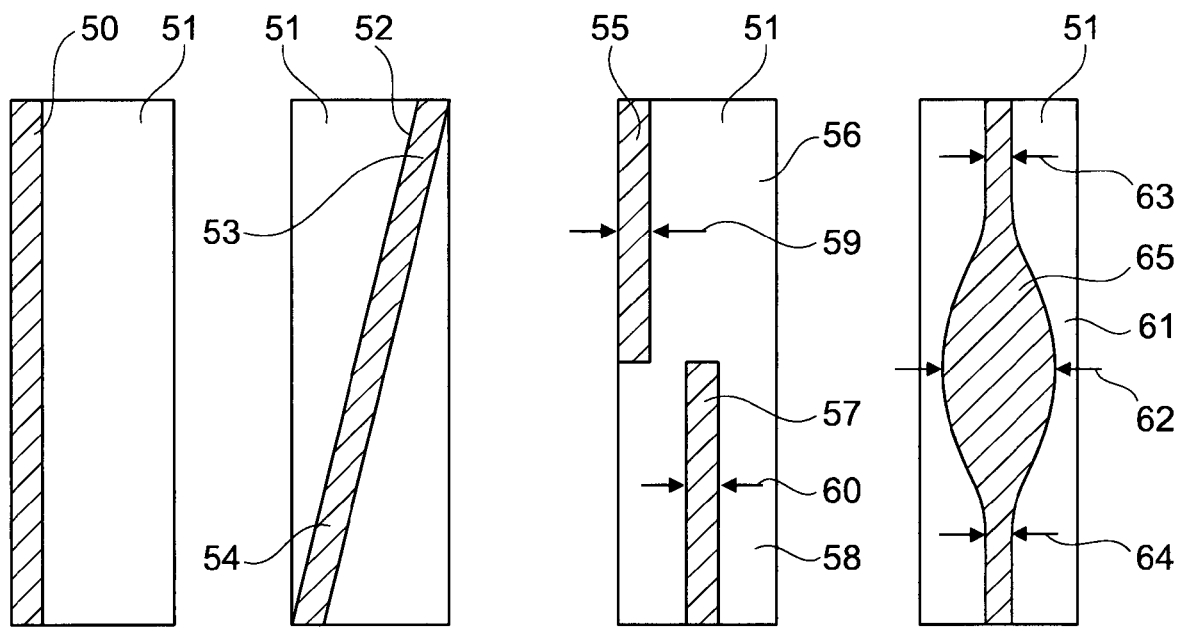

FIG. 3 shows a sketch of a 2D X-ray projection image 51 of the X-ray detector 9, wherein a selected partial area 50, represented as a dotted line, is arranged on the left edge of the 2D X-ray projection image 51. The second panoramic layer image 2 is therefore calculated by only using the selected partial areas 50 of the individual 2D X-ray projection images 51. The main radiation directions would also be shifted as a result. Within the 2D X-ray projection image 51 of the X-ray detector 9, other partial stripes can also be selected that can for example also be overlapping, in order to calculate other panoramic layer images. The 2D X-ray projection image 51 of the X-ray detector 9 could for example be split into 40 parallel partial stripes, so that 40 different panoramic layer images can be calculated. In an embodiment, the user could then scroll through the various panoramic layer images, wherein the radiation direction is varied accordingly. In this manner, the opening of the inter-dental contacts can then be graphically retraced. The user could then manually select an appropriate panoramic layer image with a sufficiently opened inter-dental contact.

FIG. 4 shows a sketch of a further embodiment with a selected partial area 52 in the form of diagonally arranged partial stripe. In the upper area 53 of the partial stripe, the main radiation direction of the partial stripe 53 is therefore shifted to the right in relation to the initial main radiation direction of the 2D X-ray projection image 51, wherein in the lower area 54, the main radiation direction of the partial stripe 53 is shifted to the left in relation to the initial main radiation direction of the 2D X-ray projection image 51. This simulates a diagonally arranged X-ray detector.

FIG. 5 shows a sketch of a further embodiment, wherein the selected partial area comprises a first partial stripe 55 in the upper area 56 of the 2D X-ray projection image 51 and a second partial stripe 57 in the lower area 58 of the 2D X-ray projection image 51. In this manner, the main radiation direction in the upper area of the 2D X-ray projection image 51, that is to say in the area of the upper jaw, is shifted to the left, wherein the main radiation direction in the lower area of the 2D X-ray projection image 51, in the area of the lower jaw, remains essentially unchanged in relation to an initial main radiation direction of the 2D X-ray projection image 51. A first width 59 of the first partial stripe 55 and a second width 60 of the second partial stripe 57 define the width of the focal layer 22 in the second calculated panoramic layer image 2.

FIG. 6 shows a further embodiment on which the selected partial area is in the shape of a stripe 65 having a variable width, wherein in the center area 61 of the 2D X-ray projection image 51 a first width 62 is dimensioned greater than a second width 63 in the upper area of the 2D X-ray projection image 51 and a third width 64 in the lower area of the 2D X-ray projection image 51. As a result, the focal layer 22 in the second panoramic layer image 2 is narrower in the center area than in the upper or lower area. As a result, the teeth in the center area can be rendered with greater separation from foreign structures than objects in the upper and lower area.

Figure 7:
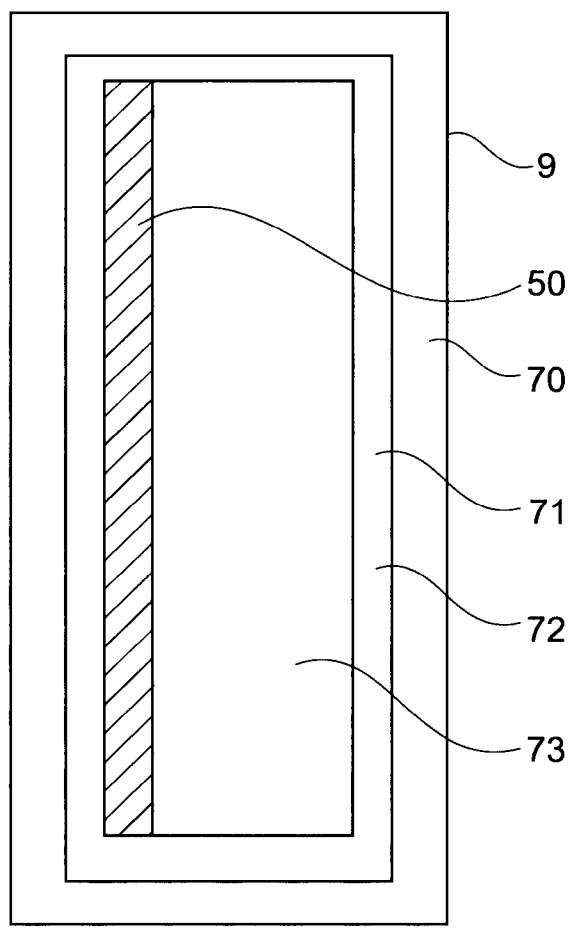

FIG. 7 shows a sketch of an X-ray detector 9, comprising a frame 70 and a sensor area 71, wherein the sensor area 71 comprises an unused and/or inactive area 72 and a used and/or active sensor area 73. The 2D X-ray projection image 51 is therefore recorded with the active sensor area 73. A partial area 50, shown as a dotted line, is selected from the image data of the recorded 2D X-ray projection image 51. The active sensor area 73 can also have the same size as the sensor area 71. There is consequently no inactive sensor area 72 on such an embodiment.

REFERENCE SYMBOLS 1 first panoramic layer image
2 second panoramic layer image
3 imaged object
4 jaw
5 patient's head
6 radiation beam of X-rays
7 X-ray source
8 radiation direction of the radiation beam
9 X-ray detector
10 arrow for the circumferential path of the X-ray detector
11 arrow for the circumferential path of the X-ray source
12 individual teeth of the jaw
13 first contact point of the incisors
14 incisors
15 arrow for rendering the overlap of the teeth
16 computer
17 first center optimized radiation direction
18 second contact point of the incisors
19 second optimized radiation direction
20 third contact point of the incisors
21 third optimized radiation direction
22 width of the focal layer
23 area of the molars
24 arrow
25 arrow
26 arrow
27 keyboard
28 mouse
29 display apparatus
30 cursor
31 first virtual tool
32 second virtual tool
40 first area
41 enlarged section of the first area
42 second area
43 enlarged section of the second area
44 third area
56 enlarged section of the third area
50 selected partial area
51 2D X-ray projection image
52 selected partial area
53 upper area of the partial stripe
54 lower area of the partial stripe
55 first partial stripe
56 upper area of the 2D X-ray projection image
57 second partial stripe
58 lower area of the 2D X-ray projection image
59 first width of the first partial stripe
60 second width of the first partial stripe
61 center area of the 2D X-ray projection image
62 first width in the upper area of the 2D X-ray projection image
63 second width in the upper area of the 2D X-ray projection image
64 third width in the lower area of the 2D X-ray projection image
65 stripe having a variable width
70 frame
71 sensor area
72 unused and/or inactive sensor area
73 used and/or active sensor area

The invention claimed is:

1. Method for generating a panoramic layer image, of an object to be imaged, by employing a 2D panoramic X-ray device, wherein the object is imaged by projecting X-rays generated by an X-ray source through the object in a radiation direction and recording said X-rays with an X-ray detector, wherein several 2D X-ray projection images are continuously recorded from various imaging directions while the X-ray source and the X-ray detector move around the object, wherein at least one panoramic layer image is calculated from the recorded 2D X-ray projection images by means of a reconstruction method, wherein the panoramic layer image is calculated by selecting and using at least one partial area from at least two 2D X-ray projection images in relation to an active sensor area wherein a selection of the at least one partial area within the 2D X-ray projection image changes a width of a focal layer of the calculated panoramic layer image, and wherein the adjustment of the main radiation direction of the particular 2D X-ray projection images is achieved by selecting the at least one partial area and therefore achieving the adjustment of the center local radiation direction of the focal layer and/or the adjustment of the width of the focal layer as a function of the imaged anatomical structures of the object.

2. Method according to claim 1, wherein the size of the at least one partial area is no greater than 80% or no greater than 40% of the particular 2D X-ray projection image.

3. Method according to claim 1, wherein a weighting function is applied on the image data of the at least one selected partial area, wherein the weighted partial areas are used for calculating the panoramic layer image.

4. Method according to claim 1, wherein the at least one partial area is a partial stripe having a fixed width or a variable width.

5. Method according to claim 1, wherein the at least one partial area is predefined for all 2D X-ray projection images with respect to its position in relation to the actively irradiated sensor area, with respect to its size, and with respect to its shape, or is variable for different 2D X-ray projection images.

6. According to claim 1, the at least one partial area is selected manually by the user or automatically by employing an algorithm.

7. Method according to claim 1, wherein the selection of the at least one partial area within the 2D X-ray projection images causes at least one main radiation direction of the particular 2D X-ray projection image and thereby a main radiation direction to be adjusted to an associated local position of the focal layer of the calculated panoramic layer image.

8. Method according to claim 1, wherein the adjustment of the main radiation direction of the particular 2D X-ray projection images is achieved by the selection of the partial areas and thereby achieving the adjustment of the main radiation direction of the focal layer to the opening of inter-dental contacts, wherein contact points between the teeth are determined and predefined and an appropriate center optimised radiation direction is determined for the particular position of the focal layer, such that the teeth have as little as possible, or no, overlaps in the particular contact area within the calculated panoramic layer image.

9. Method according to claim 1, wherein a first panoramic layer image is calculated from the individual 2D X-ray projection images, wherein the complete image information of the 2D X-ray projection images is used for the calculation, wherein a second panoramic layer image is calculated from the individually selected partial areas of the 2D X-ray projection images.

10. Method according to claim 9, wherein a difference between an actual radiation direction of the first panoramic layer image and an optimised radiation direction of the second panoramic layer image is used to automatically determine overlapping tooth regions and to graphically highlight the latter in a graphical rendering of the first and/or second panoramic layer image.

11. Method according to claim 9, a user employs a control device to toggle between a graphical rendering of the first panoramic layer image and the second panoramic layer image.

12. Method according to claim 9, wherein a user employs a control device to select an area in a graphical rendering of the first panoramic layer image, wherein an enlarged rendering of this area from the second panoramic layer image is superimposed in the manner of a magnifying glass function.

13. Apparatus for executing the method according to claim 1, comprising a computer, the X-ray source, the X-ray detector, a support arm for moving the X-ray source and the X-ray detector around the imaged object, wherein the X-ray detector has an actively irradiated sensor width between 5 mm and 40 mm, wherein the computer employs a selection algorithm to select at least one partial area of the 2D X-ray projection image and uses a calculation algorithm to calculate the panoramic layer image.

* * * * *